United States Patent [19]

Kötzsch et al.

[11] Patent Number: 4,789,752
[45] Date of Patent: Dec. 6, 1988

[54] METHOD FOR THE PREPARATION OF ORTHOESTERS OF TITANIUM, ZIRCONIUM OR HAFNIUM

[75] Inventors: Hans-Joachim Kötzsch, Rheinfelden; Hans-Günther Srebny, Stolzenau; Hans-Joachim Vahlensieck, Weir, all of Fed. Rep. of Germany

[73] Assignee: Huels Troisdorf Aktiengesellschaft, Troisdorf, Fed. Rep. of Germany

[21] Appl. No.: 878,198

[22] Filed: Jun. 25, 1986

[30] Foreign Application Priority Data

Jun. 27, 1985 [DE] Fed. Rep. of Germany ....... 3522904

[51] Int. Cl.$^4$ ............................. C07F 7/00; C07F 7/28
[52] U.S. Cl. .......................................... 556/54; 556/56
[58] Field of Search ..................................... 556/54, 56

[56] References Cited

U.S. PATENT DOCUMENTS

| 2,187,821 | 1/1940 | Nelles | 556/54 |
| 2,654,770 | 10/1953 | Herman | 556/54 |
| 2,663,720 | 12/1953 | Hill | 556/54 |
| 2,684,972 | 7/1954 | Haslam | 556/54 |
| 2,977,378 | 3/1961 | Kasper | 556/54 X |
| 3,119,852 | 1/1964 | Gilsdorf | 556/54 |
| 3,418,348 | 12/1968 | Shepard et al. | 556/54 X |
| 3,547,966 | 12/1970 | Marble | 556/54 X |
| 3,641,079 | 2/1972 | Termin et al. | 556/54 X |
| 3,754,011 | 8/1973 | Hoch | 556/54 X |
| 3,772,355 | 11/1973 | Merz | 556/54 X |
| 4,039,567 | 8/1977 | Kötzsch et al. | 556/471 |
| 4,506,087 | 3/1985 | Fischer et al. | 556/471 |

FOREIGN PATENT DOCUMENTS 2033373 4/1971 Fed. Rep. of Germany ........ 556/54 UX
997892 7/1965 United Kingdom .......... 556/54 UX Primary Examiner—Paul F. Shaver
Attorney, Agent, or Firm—Felfe & Lynch

[57] ABSTRACT

The present invention relates to the esterification of the halides of titanium, zirconium or hafnium. The esterification takes place in two steps. The first step is performed in the absence of acid acceptors, and the alcohol is introduced into the metal halide dissolved in a solvent, without any appreciable contact with the gas phase. The reactor must be held at the boiling temperature. In this step at least half of the alcohol needed for the entire reaction is used. The second esterification step is performed in a known manner with the addition of acid acceptors after the hydrogen halide that formed in the first esterification step has been removed.

16 Claims, No Drawings

METHOD FOR THE PREPARATION OF ORTHOESTERS OF TITANIUM, ZIRCONIUM OR HAFNIUM

BACKGROUND OF THE INVENTION

The subject matter of the present invention is a method for the preparation of alkyl orthoesters of titanium, zirconium or hafnium by the esterification of the tetrahalides with aliphatic alcohols in two steps.

The known methods for the preparation of orthoesters, especially of the metals titanium, zirconium and hafnium, avail themselves exclusively, even on a large technical scale, of the reaction of the corresponding tetrachlorides with aliphatic alcohols in the presence of amines as acid acceptors and solvents as diluents (cf. U.S. Pat. No. 2,187,821). This method yields usable products, yet it involves some serious disadvantages. A very special disadvantage is the great and unavoidable production of unsalable amine hydrochlorides. Moreover, the titanium and zirconium orthoesters thus prepared contain, in addition to the solvent and alcohol residues usually still present, considerable amounts of polymers. These form on the basis of the formation of alkyl halide, occuring as a secondary reaction, in which water is simultaneously formed, which has a hydrolyzing effect on the metal ester along with a simultaneous, quality-degrading formation of metal oxane.

In order at least to lessen the unavoidable production of salts, it is proposed in British patent 997,892 to esterify the titanium tetrachloride directly with the evolution of gaseous hydrogen halide, and then using a vacuum to remove the hydrogen halide. This method of direct esterification with aliphatic alcohols, however, does not result in the orthoester, but only reaches the dihalogen diester (semiester) and then stops, even when there is an excess of alcohol. The introduction of the last two alkoxy groups in the preparation of the orthoesters must, in this procedure, take place in a second step in the presence of amines. In this procedure the disadvantage of the known methods--the tendency toward the secondary reaction that forms alkyl halide and water and thus the formation of polymers in the esterification products--is not eliminated. And this problem was not been resolved, too, by the application of solvents and/or boiling the reaction mixture after the introduction of the compounds and/or complicating the process by bubbling through inert gases as proposed in British Pat. No. 987,892. Therefore these since 1963 created methods are not in large scale application up today. Especially titanium esters and zirconium esters are useful in many ways on account of their properties, and have a permanent place in a number of applications. For example, they serve as catalysts and co-catalysts for the polymerization and copolymerization of olefins, vinyl chloride, styrene, dienes, vinyl ethers, epoxides, alkylene oxides, and aldehydes, as esterification and transesterification catalysts in organic, organic silicon and organic metal monomer chemistry, and in the preparation of saturated and unsaturated polyesters, polyester amides and imides, and polyamides by means, for example, of the condensation and polyaddition reactions; in lacquers and resins as binding agent, for thixotropication, for the modification of rheological properties, and as fabricating adjuvants; for the surface treatment of glass and mineral substances; as processing agents for textiles, leather and paper, for example, especially for binding, repellentizing or delustering; for the manufacture of special ceramics, as adhesive components in adhesives, and in the manufacture of glass fiber-reinforced plastics, etc.

The problem therefore arises of finding a more efficient method of preparation, in which the above-described secondary reactions occur to a minor extent or not at all, so that orthoesters are obtained very free of polymers, and in which there is only a markedly reduced creation, if any, of ammonium halides or amine hydrochlorides.

THE INVENTION

As to the solution to this problem a method for the preparation of the orthoesters of titanium, zirconium or hafnium has been found which is accomplished in two esterification steps. In the first esterification step, metal tetrahalides in solvent are partially esterified with alcohols in the absence of acid acceptors, with the splitting off and escape of hydrogen halide. The second step completes the esterification using known procedures with the aid of acid acceptors. The first esterification step is characterized by the introduction of the alcohol into the boiling solvent such that no appreciable contact with the gas phase (containing hydrogen halide) takes place. The metal halide is first placed in the reactor in mixture with the solvent boiling, or is introduced into the boiling solvent in the same manner as the alcohol, in the molar ratio necessary for the formation of the desired ester. The second esterification step is performed after hydrogen halide has been split off and no longer escapes from the mixture, by the addition of acid acceptors, in a manner known in itself. In spite of the prior art the method according to this invention—consequentially avoiding the contact between the alcanol and the hydrohalogined and consequentially boiling the reaction mixture from the beginning of the addition of the reaction compounds—surprisingly excludes this disadvantage previously described for the known methods to give now polymer-free products and is now applicated for large-scale.

Optionally, the desired ester is the onthoester. The claimed process renders also possible to obtain partial esters, where only 2 to 4 ester groups are bound to the central metal alone, whereas the remaining valencies of the central metal atom are bound to halogen. Therefore, in the first estiofication step the quantity of the added alcohol corresponds to that ester which formation is desired.

The tetraalkyl esters of titanium, zirconium or hafnium prepared by the method of the invention, e.g., tetraethoxytitanium, tetraethoxyzirconium, tetra-n-propoxy titanium, zirconium and hafnium, tetra-n- and -isobutoxy titanium, zirconium and hafnium, tetra-2-ethylhexylorthotitanate, tetraoctadecyltitanate, etc., are obtained in yields of more than 90%, and, in comparison with the conventional methods, in a very pure form that suffices for most applications, so that in some cases distillation of the products for sale and use is unnecessary.

Starting substances for this method according to the invention are, on the one hand, the tetrachlorides, tetrabromides and tetraiodides of titanium, zirconium or hafnium, and, on the other hand, primary or secondary aliphatic, saturated and unsaturated alcohols such as, for example, methanol, ethanol, n- and iso-propanol, allyl alcohol, n-, iso- and secondary butanol, cyclopentanol, amyl alcohols, cyclohexanol, 2-ethylhexanol, octanols, nonanols, decanols, dodecyl alcohol, cetyl alcohol, octadecanol, oleanol, isoborneol, menthol, etc.

Suitable inert media for the method according to the invention are aliphatic, aromatic and/or chlorinated hydrocarbons. In particular, they are, for example, the pentanes, hexanes, heptanes, isooctane, cyclohexane, methylcyclohexane, benzine fractions such petroleum ether or ligroin, benzene, toluene, the xylenes, methylene chloride, chloroform, carbon tetrachloride, trans-dichloroethylene, trichloroethylene, perchloroethylene, chlorobenzene, the dichlorobenzenes, the trichloroethanes, trichlorotrifluoroethane, 1,1,1,3-tetrachloropropane etc.

In the procedure according to the invention, in the first reaction step the alcohol is introduced into the reaction medium in such a manner that it virtually does not come in contact with the gaseous phase above the reaction medium. In all variants of the method, the reactor always contains the inert medium, which generally consists of the solvents mentioned above. Preferably the alcohol is introduced by means of a subsurface introduction tube or other similar adding means, directly into the liquid medium; it is also sufficient, however, if the alcohol leaves the introduction tube at a point close to the surface of the liquid medium.

In the first reaction step, at least enough alcohol is fed into the reaction medium as is necessary for the attainment of the intended degree of esterification or can be achieved without the addition of acid acceptors. In general, this is at least 2 moles of alcohol per mole of metal halide. However, even in the first step of the process it is possible to feed in the entire amount of alcohol necessary for complete esterification. This is the preferred method of procedure, in which accordingly 2 to 4 mole-equivalents of the alcohol are put in in this step of the process.

During the first step, the liquid phase must be kept at the boiling temperature, so that the hydrogen halide that forms will immediately be removed. The metal halides and the partial esterification products of the first esterification step tend to fix hydrogen halid and alcohols. Surprisingly, at elevated temperatures, fixation of the alcohols but no fixation of the hydrogen halid takes place, whereas alcohols in excess remain fixed at these partial esterification products. Furthermore is has been found surprisingly that, in spite of elevated temperatures, neither the alcohols nor the esters that have formed tend to enter the secondary reactions that are known and undesirable according to the former state of knowledge. The boiling temperature will depend, of course, on the solvent selected and the alcohol that is to be used.

The metal halide to be reacted is fed to the reaction medium either together with the alcohol in the same manner as the latter, or it is first placed in the reactor together with the solvent. In the case of simultaneous introduction with the alcohol, it is advantageous to conduct the feeding such that the molar ratio of metal halide to alcohol will be between 1:2 and 1:4; if titanium chloride is used, it is preferably between 1:2.8 to 1:3.2.

In the first step, 1 to 2 mole-equivalents of alcohol are reacted very rapidly and the corresponding amount of hydrogen halide is released. As soon as no more hydrogen halide forms, an acid receptor is added to the reaction mixture, by means of which the reaction is terminated. The amount of acid acceptor to be added is based on the degree of the reaction that has preceded. In general, therefore, a maximum of 2 mole-equivalents of the acid acceptor will suffice for the completion of the reaction.

Suitable acid acceptors for this purpose are known basic compounds such as amines or ammonia.

After the addition of the acid acceptors the esterification is continued in a manner known in itself. In some cases, the remaining amount of alcohol necessary for the complete esterification must still be added if, in the first esterification step, the molar ratio of metal halide to alcohol was less than 1:4.

In practice, the method of the invention is practiced in a normal stirrer reactor with reflux condenser, under moisture-free conditions. The solvent or suspension medium is placed first in the reactor, together with the metal halide if desired, heated to the boiling temperature, and finally the alcohol is fed in in the manner described above while the reaction mixture is constantly boiling. The hydrogen halide that forms is removed in gas form from the apparatus through the reflux condenser. Then, in a manner known in itself, with a supplementary addition of alcohol to make a total of 4 equivalents, if necessary, further esterification to the orthoester is performed by the addition of appropriate amounts of acid acceptors, while the remaining halogen precipitates in the form of ammonium halides or amine hydrochlorides. The final processing is performed by the usual methods of separating the solids and, if desired, distillation.

The method according to the invention is practiced preferably at standard pressure, but the use of a vacuum can be considered. Care is to be taken, however, to see that the reaction mixture is constantly being refluxed, at least during the first esterification step.

EXAMPLES

The following examples will explain the invention without, however, restricting its scope. After the first reaction step is completed, the chlorine content of the reaction mixture is always determined in order to demonstrate the effectiveness of the procedure according to the invention. The above-mentioned secondary reactions of the hydrogen halide with the alcohol and their consequential reaction can be virtually avoided on the basis of the immediate removal of the hydrogen halide that forms. The orthoester that is obtained therefore does not have the disadvantageous properties of the products which are made according to the state of the art: it is virtually colorless and is not contaminated with metal oxanes.

EXAMPLE 1

The reaction apparatus consisted of a heated 250-ml multi-necked flask which is provided with a stirrer, internal thermometers, a reflux condenser with a deep freezer attached (dry ice and methanol), as well as two feed tubes extending below the surface of the liquid in the reactor. 58.25 g of hexane is placed in the apparatus and refluxed. 47.5 g of titanium chloride (0.25 mol) and 23 g of ethanol (0.5 mol) was fed through the two tubes over a period of 8 minutes, and then another 23 g of ethanol (0.5 mol) was fed in. At the beginning of the reaction a vigorous evolution of hydrogen chloride occurred. The temperatur below the water cooler dropped to 61° C.

After cooling, 134 g of a yellowish suspension was obtained. A sample was taken and all volatile components were removed in vacuo. Analysis of the solid residue showed: Titanium: 18.0%, chlorine: 28.4%.

This corresponds to a Ti:Cl ratio of 1:2.1 and signifies that about 47% of the chlorine was removed in the form of gaseous hydrogen chloride. Then a reaction was performed with ammonia to produce the orthoester.

EXAMPLE 2

The reaction apparatus consisted of a heated 2-liter multinecked flask with stirrer, internal thermometer, two tubes and a column head which permitted removal of the distillate. A cold trap was connected to the head of the column. 446 g of hexane was placed in the reactor and boiled with refluxing. Through the two tubes 380 g of titanium chloride (2 mol) and 279 g of ethanol (6.06 mol) were fed for 48 minutes such that the ratio of titanium chloride to ethanol amounted always to about 1:3. While this was in progress three samples of distillate were taken. The ethanol content was less than 0.1% in each case (GC area percentage). After cooling a yellowish white precipitate separated. A sample of the dried product contained 27.8% chlorine. The liquid phase contained 0.63% chlorine. This signifies that, during the first phase of the reaction, about 49% of the chlorine present was removed from the reaction mixture in the form of hydrogen chloride.

EXAMPLE 3

In a reaction apparatus as described in Example 1, but with a two-liter flask, 446 g of hexane was placed and heated to boiling. Through the two tubes 380 g of titanium chloride (2 mol) and 360 g of n-propanol (6 mol) were fed for 47 minutes such that the ratio of titanium chloride to n-propanol amounted always to about 1:3. At the beginning of the addition of these substances a vigorous formation of hydrogen chloride immediately began. The temperature below the water cooler dropped to 60° C. and rose toward the end of reaction up to 64° C. A sample was taken from the bottom of the column and the hexane was removed in vacuo. The analysis of the residue shows: titanium 16.2%, chlorine 23.8% (Ti:Cl molar ratio =1:1.99). After the addition of another 120 g of n-propanol (2 mol) the mixture was reacted in the known manner with ammonia to yield the orthoester.

EXAMPLE 4

The reaction apparatus consisted of a heated 500 ml multinecked flask which was provided with a stirrer, internal thermometers, a reflux condenser connected to a deep freezer (dry ice/methanol) and a dropping funnel. The bottom end of the dropping funnel consisted of a tube whose end reached below the surface of the liquid phase of the reactor contents. 150 ml of heptane and 47.5 g of titanium chloride (0.25 mol) was placed in the reactor and heated at ebullition. Over a period of 68 minutes, 30 g of isopropanol (0.5 mol) was added through the feed tube. Hydrogen chloride began at once to evolve and the temperature below the water cooler dropped to 94° C. After the reaction had ended a white precipitate formed during cooling.

A sample of the precipitate was dried and analyzed. The ratio of titanium to chloride in this sample was 1:2.37. This meant that 1.63 mol of hydrogen chloride, i.e., about 41% of the total chlorine, had been removed during the reaction.

After the addition of ammonia and another 30 g of isopropanol the entire mixture was then reacted to form the orthoester in a manner known in itself.

EXAMPLE 5

The reaction apparatus consisted of a heated two-liter double-walled flask which was provided with a stirrer, internal thermometer, a reflux condenser with a deep freezer connected, as well as two introduction tubes. 446 g of heptane was placed in the reactor and refluxed. Then over a period of 80 minutes 380 g of titanium chloride (2 mol) and 360 g of isopropanol (6 mol) were introduced such that the ratio of titanium chloride to isopropanol amounted to between 1:2.4 and 1:3. At the start of the reaction a vigorous evolution of hydrogen chloride immediately began. The temperature below the water cooler dropped to a maximum of 86° C. After the addition of another 120 g of isopropanol (2 mol), 1195 g of a solution was obtained having a chlorine content of 16.1%. This meant that approximately 32% of the chlorine present had been removed in the form of hydrogen chloride.

EXAMPLE 6

In a reaction apparatus as described in Example 2, 446 g of hexane was placed and refluxed. Through the two tubes titanium chloride and iscpropanol were introduced in a 1:3 ratio. During this period three samples of distillate were taken in each experiment. The isopropanol content was 4% maximum (GC area percentage). After cooling, a sample was taken and analyzed. The amount of hydrogen chloride removed was between 27% and 33%. The experimental parameters are listed in Table 1.

TABLE 1

| | Experimental Parameters | | | |
|---|---|---|---|---|
| Experiment | Moles of titanium chloride | Moles of isopropanol | Feed time in min. | % of HCl removed |
| 1 | 2 | 6 | 44 | 30.0 |
| 2 | 2 | 6 | 45 | 32.5 |
| 3 | 2 | 6 | 42 | 28.5 |
| 4 | 2 | 6 | 45 | 27.5 |
| 5 | 2 | 6 | 44 | 31.25 |

EXAMPLE 7

The reaction apparatus consisted of a heated 500-milliliter multi-necked flask which was equipped with stirrer, internal thermometer, reflux condenser with deep freezer (dry ice/methanol) attached, and an injector driven with nitrogen. A dropping funnel was connected to the injector. The bottom end of the injector reached below the surface of the liquid in the reactor. 95 g of titanium chloride (0.5 mol) and 300 ml of heptane were placed in the reactor and heated to ebullition. Over a period of about 1 hour, 74 g of n-butanol (1 mol) was fed in through the injector. The temperature below the water cooler dropped to 65° C. and rose during the reaction back to 75° C. After cooling, the heptane was removed in vacuo. 130 g of $(n-BuO)_2TiCl_2$ was obtained as a yellow, highly viscous liquid.

Ti: 18.1%, Cl: 27.5%.

EXAMPLE 8

The reaction apparatus described in Example 4 was used, but with a two-liter flask. 669 g of heptane and 570 g of titanium chloride (3 mol) were placed in the reactor and heated to ebullition. Over a period of 90 minutes, 888 g of n-butanol (12 mol) was fed in through the tube. At the beginning of the addition of the n-butanol a vigorous evolution of hydrogen chloride immediately started. The temperature below the water cooler dropped from 101° C. to 88° C. and rose to about 92° C. toward the end of the reaction.

After cooling, 1889 g of a liquid was obtained having a chlorine content of 12.3%. This means that about 45% of the chlorine present had been removed in the form of gaseous hydrogen chloride.

Then, in a known manner, the reaction to form the orthoester was performed with ammonia.

EXAMPLE 9

The reaction apparatus described in Example 8 was used, but the tube at the bottom of the dropping funnel reached to a point just above the surface of the liquid. 446 g of heptane and 380 g of titanium chloride (2 mol) were placed in the reactor and heated at ebullition. Over a period of 42 minutes, 595 g of n-butanol (8.04 mol) was added. A violent reaction occurred immediately at the start of the addition. The temperature below the water cooler dropped from 102° C to 90° C. After cooling, 1236 g was obtained of a liquid with a chlorine content of 12.2%. This meant that about 47% of the chlorine present had been removed in the form of hydrogen chloride. In a known manner, a reaction was then performed with ammonia to form the orthoester.

EXAMPLE 10

The reaction apparatus consisted of a heated 250-ml multinecked flask which was provided with stirrer, internal thermometer, reflux condenser with deep freezer attached (dry ice/methanol) as well as two feed tubes. Two dropping funnels were connected to the two tubes. The tubes reached below the surface of the liquid in the reactor. 58.25 g of hexane was placed in the reactor and refluxed. Through the two feed tubes a total of 47.5 g of titanium chloride (0.25 mol) and 74 g of n-butanol (1 mol) was feed for a period of 37 minutes such that the ratio of titanium chloride to n-butanol amounted to about 1:3. A strong reaction took place right at the start of the addition of the n-butanol. The temperature below the water cooler dropped down to 63° C. After the addition of titanium chloride had ended, the titration of a sample of the reaction mixture showed that 47.8% of the chlorine had been removed in the form of hydrogen chloride. After the rest of the n-butanol had been added, 159 g was obtained of a liquid containing 7.8% titanium and 12.1% chlorine.

In a known manner, the mixture was then reacted with ammonia to the orthoester.

EXAMPLE 11

In a reaction apparatus as described in Example 6, 446 g and 557.5 g of hexane, respectively, was placed and refluxed. Through the two feed tubes titanium chloride and n-butanol were introduced in a ratio of 1:3. While this was in progress three samples of the distillate were taken in each case. The butanol content was always less than 0.1% (GC area percentage). After cooling, a sample was taken and analyzed. The amount of hydrogen chloride removed was always greater than 445. The experimental parameters are listed in Table 2.

TABLE 2

| | Experimental Parameters | | | | |
|---|---|---|---|---|---|
| Experiment | Moles of titanium chloride | Moles of n-butanol | Feed time minutes | % of HCl removed | Butanol content in the distillate |
| 1 | 2 | 6 | 47 | 44.4 | n.d. |
| 2 | 2 | 6 | 50 | 46.0 | n.d. |
| 3 | 2.5 | 7.5 | 50 | 44.1 | n.d. |
| 4 | 2.5 | 7.5 | 45 | 45.4 | <0.1 |
| 5 | 2 | 6 | 45 | 44.0 | n.d. |
| 6 | 2 | 6 | 42 | 46.0 | n.d. | n.d. = not detectable

These examples also prove, that the excessive butanol, not needed to form the partial esterification product is fixed to the formed partial ester product, whereas the hydrogen halid is not fixed to this ester under the conditions according to this invention.

These examples also proove that the excessive butanol, not needed to form the partial esterification product is fixed to the formed partial ester product, whereas the hydrogen halid is not fixed to this ester under the conditions according to this invention.

EXAMPLE 12

The reaction apparatus decribed in Example was used. In addition, an apparatus for stabilizing vacuum (Brandt) was connected. 223 g of benzine (boiling range 100° to 140° C.) and 190 g of titanium chloride (1 mol) were placed in the apparatus and the apparatus was evacuated down to 400 mbar.

Then the mixture was heated at ebullition. The temperature at the bottom was 86° C. and below the water cooler it was 54° C. A total of 303 g of n-butanol (4.1 mol) was fed into the mixture through the tube. Immediately at the start of the feeding of the alcohol the formation of hydrogen chloride began. After the reaction had ended and the mixture was cooled, 641 g of a solution was obtained which had a chlorine content of 11.1%. This signified that 50% of the chlorine had been removed in the form of hydrogen chloride. In a known manner, the mixture was then reacted with ammonia to the orthoester.

EXAMPLE 13

The reaction apparatus consisted of a heated enameled vessel of two cubic meters capacity, equipped with three feed tubes, a stirrer, and a glass condenser operated with water and connected to a 4 square meter Hastelloy C brine cooler (−45° C.). 670 liters of hexane were placed in it and refluxed. The temperature below the water condenser amounted to 69° C. Over a period of 2 hours 380 kg of titanium chloride (2 kmol) and 444 kg of n-butanol (6 kmol) were put in at such a rate that the molar ratio of titanium chloride to n-butanol amounted always to about 1:3. Immediately at the start of the addition a vigorous evolution of hydrogen chloride began. The temperature below the water condenser dropped to 60° C. and rose toward the end of the reaction back to 64° C. After the reaction another 155.4 kg of n-butanol (2.1 kmol) was added with stirring. A sample had a chlorine content of 11.6%. This meant that 47.5% of the chlorine present had been removed in the form of hydrogen chloride. After cooling to about 30° C., the mixture was first diluted with 200 liters of hexane, and then ammonia was fed through the third feed tube for a period of 2 hours. The suspension obtained was centrifuged to separate the precipitated ammonium chloride. First the hexane was distilled out of the filtrate; then, at a vacuum of less than 1 mbar and at a head temperature of about 155° C., the butyl titanate was purified by distillation. 619 kg of butyl titanate was obtained.

Gardner number: <1
Titanium content: ≤14%.

It will be understood that the specification and examples are illustrative but not limitative of the present invention in that other embodiments within the spirit and scope of the invention will suggest themselves to those skilled in the art.

What is claimed is:

1. A method for the preparation of alkyl orthoesters of titanium, zirconium or hafnium in two esterification steps, wherein, in the first esterification step, titanium, zirconium or hafnium tetrahalides are partially esterified with alcohols in the absence of acid acceptors, in the presence of a solvent, with the splitting off of hydrogen halide, and then the esterification is completed with the aid of acid acceptors, said first esterification step comprising introducing the alcohol into boiling solvent containing the tetrahalides in a manner such that no appreciable contact with the gas phase above the boiling solvent takes place, and in a molar ratio of tetrahalide to alcohol of between 1:2 to 1:4, and the second esterification step comprises completing the esterification by adding acid acceptors to the solvent mixture after the hydrogen halide has been split off.

2. The method of claim 1 wherein the tetrahalide is introduced into the solvent before it is heated to boiling.

3. The method of claim 1 wherein the tetrahalide is introduced into the boiling solvent in a manner such that no appreciable contact with the gas phase above the solvent takes place.

4. The method of claim 1 wherein the second step is commenced when hydrogen halide is no longer released from the reaction.

5. The method of claim 1 wherein the acid acceptors are amines or ammonia.

6. The method of claim 1 wherein the alcohol is methanol, ethanol, n- and iso-propanol, allyl alcohol, n-, iso- and secondary butanol, cyclopentanol, amyl alcohols, cyclohexanol, 2-ethylhexoanol, octanols, nonanols, decanols, dodecyl alcohol, cetyl alcohol, octadecanol, oleanol, isoborneol or methol, and the solvent is a pentane, hexane, heptane, isooctane, cylohexane, methylcyclohexane or benzine fractions such petroleum ether or ligroin, benzene, toluene, the xylenes, methylene chloride, chloroform, carbon tetrachloride, trans-dichloroethylene, trichloroethylene, perchloroethylene, chlorobenzene, the dichlorobenzenes, the trichloroethanes, trichlorotriflurorethane or 1,1,1-tetrachloropropane.

7. A method for the preparation of alkyl orthoesters of titanium, zirconium or hafnium in two esterification steps, wherein, in the first esterification step, titanium, zirconium or hafnium tetrahalides are partially esterified with alcohols in the absence of acid acceptors, in the presence of a solvent, with the splitting off of hydrogen halide, and then the esterification is completed with the aid of acid acceptors, said first esterification step comprising introducing the alcohol and the tetrahalides at the same time into boiling solvent in a manner such that no appreciable contact with the gas phase above the boiling solvent takes place, and in a molar ratio of tetrahalide and alcohol of between 1:2 to 1:4 and the second esterification step comprises completing the esterification by adding acid acceptors to the solvent mixture after the hydrogen halide has been split off.

8. The method of claim 7 wherein the second step is commenced when hydrogen halide is no longer released from the reaction.

9. The method of claim 7 wherein the acid acceptors are amines or ammonia.

10. The method of claim 7 wherein the alcohol is methanol, ethanol, n- and iso-propanol, alkyl alcohol, n-iso- and secondary butanol, cyclopentanol, amyl alcohols, cyclohexanol, 2-ethylhexanol, octanols, nonanols, decanols, dodecyl alcohol, cetyl alcohol, octadecanol, oleanol, isoborneol or methol, and the solvent is a pentane, hexane, heptane, isooctane, cyclohexane, methylcyclohexane, petroleum ether, ligroin, benzene, toluene, the xylenes, methylene chloride, chloroform, carbon tetrachloride, trans-dichloroethylene, trichloroethylene, perchloroethylene, chlorobenzene, the dichlorobenzenes, the trichloroethanes, trichlorotrifluoroethane or 1,1,1-tetrachloropropane.

11. The method of claim 7 wherein the second etherification step further comprises adding additional alcohol in an amount required to complete the esterification.

12. The method of claim 1 wherein the second etherification step further comprises adding additional alcohol in an amount required to complete the esterification.

13. The method of claim 1 wherein the alcohol contains an alkyl group of 1 to 6 carbon atoms.

14. The method of claim 7 wherein the alcohol contains an alkyl group of 1 to 6 carbon atoms.

15. The method of claim 1 wherein the alcohol contains an alkyl group of 1 to 4 carbon atoms.

16. The method of claim 7 wherein the alcohol contains an alkyl group of 1 to 4 carbon atoms.

* * * * *

UNITED STATES PATENT AND TRADEMARK OFFICE
CERTIFICATE OF CORRECTION

PATENT NO. : 4,789,752
DATED : December 6, 1988
INVENTOR(S) : Hans-Joachim Kötzsch et al It is certified that error appears in the above-identified patent and that said Letters Patent is hereby corrected as shown below:

Column 1, line 47, "compounds" should read --components--.

Column 1, line 49, "987,892" should read --997,892--.

Column 2, line 42, "onthoester" should read --orthoester--.

Column 2, line 47, "estiofication" should read --esterification--.

Column 4, line 63, "temperatur" should read --temperature--.

Column 8, line 23, following "Example" insert --8--.

Column 9, line 44, "ethylhexoanol" should read --ethylhexanol--.

Column 9, line 47, "cylohexane" should read --cyclohexane--.

Column 10, line 2, "trichlorotrifluororethane" should read --trichlorotrifluoroethane--.

Column 10, line 25, "alkyl" should read --allyl--.

Signed and Sealed this

Fifteenth Day of May, 1990

*Attest:*

HARRY F. MANBECK, JR.

*Attesting Officer*      *Commissioner of Patents and Trademarks*